US009434817B2

(12) United States Patent
Katayama et al.

(10) Patent No.: US 9,434,817 B2
(45) Date of Patent: Sep. 6, 2016

(54) ROOM-TEMPERATURE-CURABLE RESIN COMPOSITION

(71) Applicant: SHIN-ETSU CHEMICAL CO., LTD., Tokyo (JP)

(72) Inventors: Taiki Katayama, Annaka (JP); Takafumi Sakamoto, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 14/916,355

(22) PCT Filed: Jul. 10, 2014

(86) PCT No.: PCT/JP2014/003667
§ 371 (c)(1),
(2) Date: Mar. 3, 2016

(87) PCT Pub. No.: WO2015/052859
PCT Pub. Date: Apr. 16, 2015

(65) Prior Publication Data
US 2016/0194453 A1    Jul. 7, 2016

(30) Foreign Application Priority Data

Oct. 10, 2013    (JP) .................................. 2013-212662

(51) Int. Cl.
*C08G 77/08* (2006.01)
*C07F 9/22* (2006.01)

(52) U.S. Cl.
CPC ............... *C08G 77/08* (2013.01); *C07F 9/224* (2013.01)

(58) Field of Classification Search
CPC ................................. C07F 9/224; C08G 77/08
USPC ............................. 524/849; 526/279; 556/405
See application file for complete search history.

(56) References Cited

U.S. PATENT DOCUMENTS

| 4,579,963 | A | 4/1986 | Arai et al. |
| 4,587,354 | A | 5/1986 | Takago et al. |
| 8,840,993 | B2 * | 9/2014 | Yang .................... C07C 267/00 427/387 |
| 2013/0101840 | A1 | 4/2013 | Yang et al. |
| 2013/0101841 | A1 | 4/2013 | Yang et al. |

FOREIGN PATENT DOCUMENTS

| JP | S59-39897 A | 3/1984 |
| JP | S59-176349 A | 10/1984 |
| JP | S60-190457 A | 9/1985 |
| JP | 04134089 A * | 5/1992 |
| JP | H04-134089 A | 5/1992 |
| JP | 2007-204502 A | 8/2007 |
| JP | 2013-001670 A | 1/2013 |
| JP | 2013-532222 A | 8/2013 |
| JP | 2013-532223 A | 8/2013 |

* cited by examiner

*Primary Examiner* — Kelechi Egwim
(74) *Attorney, Agent, or Firm* — Oliff PLC

(57) ABSTRACT

The invention is a room-temperature-curable resin composition including a phosphazene skeleton-containing organosilicon compound shown by the following general formula (1). This provides a room-temperature-curable resin composition which is curable in short time, free from generation of an odor due to the catalyst, free from a heavy environmental load; and has sufficient hardness, elongation at shear, and tensile strength after curing.

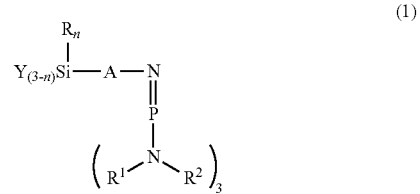

(1)

6 Claims, No Drawings

ROOM-TEMPERATURE-CURABLE RESIN COMPOSITION

TECHNICAL FIELD

The present invention relates to a room-temperature-curable resin composition, particularly a room-temperature-curable resin composition which contains an organopolysiloxane.

BACKGROUND ART

As a composition which is curable by reacting with moisture in the air to form crosslinking, a room-temperature-curable resin composition such as a room-temperature-curable organopolysiloxane composition is known conventionally. This room-temperature-curable resin composition (particularly, a room-temperature-curable organopolysiloxane composition such as a room-temperature-curable silicone rubber composition, which gives a rubber-like elastic material (elastomer) by curing) has been widely used in various fields such as building, transporters, electric and electronic components, and so on, because of its superior safety, durability as a rubber, and an adhesive property. This moisture-cure type room-temperature-curable resin composition requires a certain degree of time to be cured when it is applied to a part to be used, since it depends curing system in which crosslinking proceeds gradually by moisture in the air.

Various curing catalysts for reducing the curing time have been disclosed. Particularly, as a curing catalyst for a moisture-cure type room-temperature-curable resin composition having a hydrolysable silicon group in the molecule, dibutyl tin compounds such as dibutyl tin dilaurate, dibutyl tin diacetate are used. These organotin compounds are widely used since they enable to cure a room-temperature-curable resin composition rapidly. The organotin compounds, however, contain tin, which is heavy metal, and therefore are recently subjected to indications of risk and toxicity to the human body, and an environmental load.

Alternatively, as a curing catalyst for a room-temperature-curable resin composition, organic acid compounds such as carboxylic acids or organic base compounds such as amines are known as other organic catalyst than organotin compounds (see patent documents 1 to 5).

CITATION LIST

Patent Literature

Patent Document 1: Japanese Unexamined Patent publication (Kokai) No. 59-039897
Patent Document 2: Japanese Unexamined Patent publication (Kokai) No. S59-176349
Patent Document 3: Japanese Unexamined Patent publication (Kokai) No. S60-190457
Patent Document 4: Japanese Unexamined Patent publication (Kokai) No. 2007-204502
Patent Document 5: Japanese Unexamined Patent publication (Kokai) No. 2013-001670

SUMMARY OF INVENTION

Technical Problem

These compounds, however, cannot largely reduce the curing time. When a large amount of these compound are formulated so as to reduce the curing time, there arises a problem of generating an odor due to the catalyst. Accordingly, these compounds are utilized as a co-catalyst which is used in combination with an organotin compounds.

The present invention was accomplished to solve the foregoing problems. It is an object of the present invention to provide a room-temperature-curable resin composition which is curable in short time, free from generation of an odor due to the catalyst, free from a heavy environmental load; and has sufficient hardness, elongation at shear, and tensile strength after curing.

Solution to Problem

To solve the foregoing problems, the present invention provides a room-temperature-curable resin composition comprising a phosphazene skeleton-containing organosilicon compound shown by the following general formula (1),

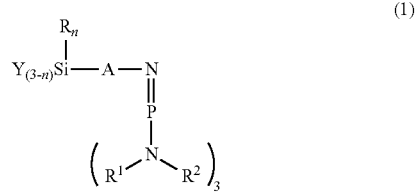

wherein, "R" represents a substituted or unsubstituted monovalent hydrocarbon group having 1 to 12 carbon atoms, "$R^1$" and "$R^2$" may be the same or different and represent a substituted or unsubstituted monovalent hydrocarbon group having 1 to 12 carbon atoms, "A" represents a single bond or a divalent hydrocarbon group having 1 to 6 carbon atoms, "Y" represents a hydrolysable group, and "n" is an integer satisfying $0 \leq n \leq 3$.

Such a room-temperature-curable resin composition can be a room-temperature-curable resin composition which is curable in short time, free from generation of an odor due to the catalyst, free from a heavy environmental load; and has sufficient hardness, elongation at shear, and tensile strength after curing.

In this case, the room-temperature-curable resin composition preferably comprises an organopolysiloxane.

Such a room-temperature-curable resin composition can be a room-temperature-curable resin composition which is curable in shorter time, and has sufficient hardness, elongation at shear, and tensile strength after curing.

In this case, the room-temperature-curable resin composition which contains the foregoing organopolysiloxane preferably comprises:
(A) 0.001 to 20 parts by mass of the phosphazene skeleton-containing organosilicon compound shown by the foregoing general formula (1);
(B) 100 parts by mass of the organopolysiloxane;
(C) 0 to 15 parts by mass of a curing catalyst except for the component (A);
(D) 0 to 30 parts by mass of either or both of hydrolysable silane and a partial hydrolysis-condensate thereof except for the component (A);
(E) 0 to 1,000 parts by mass of a filler; and
(F) 0 to 30 parts by mass of an adhesion promoter.

Such a room-temperature-curable resin composition can be a room-temperature-curable resin composition which is curable in shorter time and has an excellent adhesive property; particularly gives an elastomer-like cured product such as silicone rubber having sufficient hardness, elongation at shear, and tensile strength after curing (particularly, a room-temperature-curable organopolysiloxane composition such as a room-temperature-curable silicone rubber composition).

In this case, the room-temperature-curable resin composition is preferably used for any of a coating agent, an adhesive, and a sealant.

The room-temperature-curable resin composition of the present invention can be suitably used for a coating agent, an adhesive, or a sealant.

Advantageous Effects of Invention

As mentioned above, the room-temperature-curable resin composition of the present invention contains a particular phosphazene skeleton-containing organosilicon compound as a curing catalyst, and therefore can be a room-temperature-curable resin composition which is curable in short time even without containing an organotin compound, does not generate an odor due to the catalyst, does not burden the environment with a heavy load; and has sufficient hardness, elongation at shear, and tensile strength, that is, rubber physical properties after curing.

In addition, such a room-temperature-curable resin composition of the present invention can be suitably used for a coating agent, an adhesive, or a sealant.

DESCRIPTION OF EMBODIMENTS

As mentioned above, it is desired to develop a room-temperature-curable resin composition which is curable in short time, free from generation of an odor due to the catalyst, free from a heavy environmental load; and has sufficient hardness, elongation at shear, and tensile strength, that is, rubber physical properties after curing.

The present inventors diligently study to accomplish the above objects and consequently found that when a particular phosphazene skeleton-containing organosilicon compound is contained as a curing catalyst, it is possible to obtain a room-temperature-curable resin composition which is curable in short time, free from generation of an odor due to the catalyst, free from a heavy environmental load; and has sufficient rubber physical properties after curing, thereby brought the present invention to completion.

That is, the present invention is a room-temperature-curable resin composition (particularly, a room-temperature-curable organopolysiloxane composition which gives rubber-like elastic material (elastomer) by curing, such as a room-temperature-curable silicone rubber composition) comprising a phosphazene skeleton-containing organosilicon compound shown by the following general formula (1),

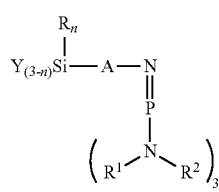 (1)

wherein, "R" represents a substituted or unsubstituted monovalent hydrocarbon group having 1 to 12 carbon atoms, "R$^1$" and "R$^2$" may be the same or different and represent a substituted or unsubstituted monovalent hydrocarbon group having 1 to 12 carbon atoms, "A" represents a single bond or a divalent hydrocarbon group having 1 to 6 carbon atoms, "Y" represents a hydrolysable group, and "n" is an integer satisfying 0≤n≤3.

Hereinafter, the present invention will be described in detail, but the present invention is not limited thereto.

The room-temperature-curable resin composition of the present invention preferably comprises:

(A) 0.001 to 20 parts by mass of the phosphazene skeleton-containing organosilicon compound shown by the foregoing general formula (1);
(B) 100 parts by mass of an organopolysiloxane;
(C) 0 to 15 parts by mass of a curing catalyst except for the component (A);
(D) 0 to 30 parts by mass of either or both of hydrolysable silane and a partial hydrolysis-condensate thereof except for the component (A);
(E) 0 to 1,000 parts by mass of a filler; and
(F) 0 to 30 parts by mass of an adhesion promoter.

[Component (A)]

The phosphazene skeleton-containing organosilicon compound of the component (A) is a phosphazene skeleton-containing organosilane compound shown by the following general formula (1),

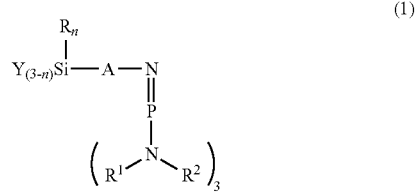 (1)

wherein, "R" represents a substituted or unsubstituted monovalent hydrocarbon group having 1 to 12 carbon atoms, "R$^1$" and "R$^2$" may be the same or different and represent a substituted or unsubstituted monovalent hydrocarbon group having 1 to 12 carbon atoms, "A" represents a single bond or a divalent hydrocarbon group having 1 to 6 carbon atoms, "Y" represents a hydrolysable group, and "n" is an integer satisfying 0≤n≤3.

In the foregoing general formula (1), illustrative examples of a substituted or unsubstituted monovalent hydrocarbon group having 1 to 12 carbon atoms represented by "R" include alkyl groups such as a methyl group, an ethyl group, a propyl group, an isopropyl group, a butyl group, an isobutyl group, a tert-butyl group, a pentyl group, a hexyl group, a heptyl group, an octyl group, a 2-ethyl-hexyl group, a nonyl group, a decyl group, and a dodecyl group; cycloalkyl groups such as a cyclopentyl group and a cyclohexyl group; alkenyl groups such as a vinyl group, an allyl group, a propenyl group, an isopropenyl group, a butenyl group, a pentenyl group, a hexenyl group, and a cyclohexenyl group; aryl groups such as a phenyl group, a tolyl group, a xylyl group, α- and β-naphtyl groups; aralkyl groups such as a benzyl group, a 2-phenylethyl group, and a 3-phenylpropyl group; and groups in which hydrogen atoms of these groups are partially or fully substituted by a halogen atom(s) such as F, Cl, and Br, or a cyano group and so on, such as a 3-chloropropyl group, 3,3,3-trifluoropropyl group, a 2-cyanoethyl group. Among them, alkyl groups such as a methyl group and an ethyl group are preferable, and a methyl group is particularly preferable.

In the foregoing general formula (1), illustrative examples of a substituted or unsubstituted monovalent hydrocarbon group having 1 to 12 carbon atoms represented by "$R^1$" and "$R^2$" include alkyl groups such as a methyl group, an ethyl group, a propyl group, an isopropyl group, a butyl group, an isobutyl group, a tert-butyl group, a pentyl group, a hexyl group, a heptyl group, an octyl group, a 2-ethyl-hexyl group, a nonyl group, a decyl group, and a dodecyl group; cycloalkyl groups such as a cyclopentyl group and a cyclohexyl group; alkenyl groups such as a vinyl group, an allyl group, a propenyl group, an isopropenyl group, a butenyl group, a pentenyl group, a hexenyl group, and a cyclohexenyl group; aryl groups such as a phenyl group, a tolyl group, a xylyl group, α- and β-naphtyl groups; aralkyl groups such as a benzyl group, a 2-phenylethyl group, and 3-phenylpropyl group; and groups in which hydrogen atoms of these groups are partially or fully substituted by a halogen atom(s) such as F, Cl, and Br, or a cyano group and so on, such as a 3-chloropropyl group, 3,3,3-trifluoropropyl group, a 2-cyanoethyl group. Among them, alkyl groups such as a methyl group and an ethyl group are preferable, and a methyl group is particularly preferable.

In the foregoing general formula (1), a divalent hydrocarbon group having 1 to 6 carbon atoms represented by "A", which represents a single bond or a divalent hydrocarbon group having 1 to 6 carbon atoms, is preferably an alkylene group, and more preferably an alkylene group shown by $-(CH_2)_p-$ or $-CH(CH_3)-(CH_2)_{p-1}-$ (herein, "p" is 1 to 6). Among them, $-CH_2-$, $-CH_2CH_2-$, $-CH(CH_3)CH_2-$, and $-(CH_2)_3-$ are particularly preferable.

In the foregoing general formula (1), "Y" represents a hydrolysable group, and illustrative examples thereof include alkoxy groups such as a methoxy group, an ethoxy group, a propoxy group, an isopropoxy group, a butoxy group, an isobutoxy group, and a tert-butoxy group; alkoxyalkoxy groups such as a methoxyethoxy group, an ethoxyethoxy group, and a methoxypropoxy group; acyloxy groups such as an acetoxy group, an octanoyloxy group, a benzoyloxy group; alkenyloxy groups such as a vinyloxy group, an allyloxy group, a propenyloxy group, an isopropenyloxy group, an 1-ethyl-2-methylvinyloxy group; ketoxime groups such as a dimethyl ketoxime group, a methyl ethyl ketoxime group, a diethyl ketoxime group; amino groups such as a dimethylamino group, a diethylamino group, a butylamino group, a cyclohexylamino group; aminoxy groups such as a dimethylaminoxy group, a diethylaminoxy group; amide groups such as an N-methylacetamide group, an N-ethylacetamide group, an N-methylbenzamide group. Among them, alkoxy groups are particularly preferable.

Further, "n" is an integer satisfying 0≤n≤3, and is preferably, 0, 1, or 2.

The foregoing phosphazene skeleton-containing organosilicon compound contained in the inventive room-temperature-curable resin composition acts as a curing catalyst for the room-temperature-curable resin composition to cure the room-temperature-curable resin composition rapidly. Accordingly, the inventive room-temperature-curable resin composition which contains the phosphazene skeleton-containing organosilicon compound as a curing catalyst can be a room-temperature-curable resin composition which is curable in short time without containing a conventionally used curing catalyst such as an organotin compound as a curing catalyst, does not generate an odor due to the catalyst, does not burden the environment with a heavy load; and has sufficient hardness, elongation at shear, and tensile strength after curing.

Naturally, the curing rate can be further improved by combined use of the phosphazene skeleton-containing organosilicon compound in the present invention and an organotin compound as a curing catalyst. In this case, the amount of the organotin compound can be reduced, and risk, toxicity, and an odor can be lowered than in the previous arts thereby.

Illustrative examples of such a phosphazene skeleton-containing organosilicon compound include N,N,N',N',N",N"-hexamethyl-N'"-[3-(trimethoxysilyl)propyl]-phosphorimidictriamide, N,N,N',N',N",N"-hexaethyl-N'"-[3-(trimethoxysilyl)propyl]-phosphorimidictriamide, N,N,N',N',N",N"-hexamethyl-N'"-(trimethylsilylmethyl)-phosphorimidictriamide which are shown by the following structural formula.

The following shows a structural formula of the foregoing N,N,N',N',N",N"-hexamethyl-N'"-[3-(trimethoxysilyl)propyl]-phosphorimidictriamide.

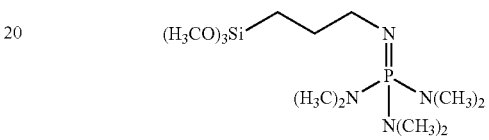

The following shows a structural formula of the foregoing N,N,N',N',N",N"-hexaethyl-N'"-[3-(trimethoxysilyl)propyl]-phosphorimidictriamide.

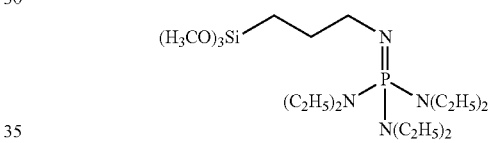

The following shows a structural formula of the foregoing N,N,N',N',N",N"-hexamethyl-N'"-(trimethylsilylmethyl)-phosphorimidictriamide.

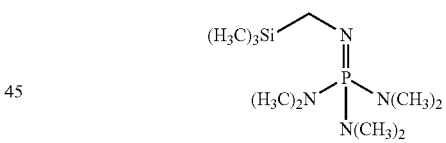

The formulation amount of the phosphazene skeleton-containing organosilicon compound is preferably 0.001 to 20 parts by mass, particularly preferably 0.01 to 5 parts by mass, based on 100 parts by mass of the organopolysiloxane of the component (B) described later. The phosphazene skeleton-containing organosilicon compound of the component (A) may be used alone or in combination of two or more kinds.

Although a polymer which is a base component (a main reagent) of the inventive room-temperature-curable resin composition is not particularly limited, it is preferable to contain an organopolysiloxane.

[Component (B)]

The organopolysiloxane of the component (B) is the main reagent (a base polymer) of the room-temperature-curable resin composition of the present invention, and has at least two hydroxyl groups (silanol groups) or hydrolysable groups bound to silicon atoms in the molecule. As these organopolysiloxane, specifically, a linear diorganopolysiloxane both terminals of which are blocked with hydroxyl groups (diorganohydroxysilyl groups) or hydrolysable groups (hydrolysable group-containing triorganosilyl groups) shown by the following general formula (2) or (3) is used.

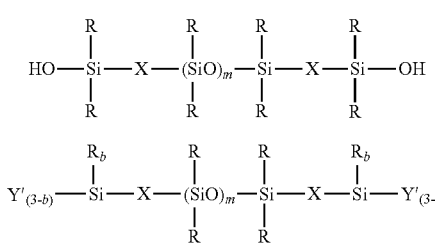

wherein, "R" has the same meaning as above, "X" represents an oxygen atom or a divalent hydrocarbon group having 1 to 8 carbon atoms, "Y'" represents a hydrolysable group, "b" is 0 or 1; and "m" is a number to make the viscosity of this organopolysiloxane at 25° C. to be 100 to 1,000,000 mPa·s, preferably an integer of 10 to 1,500, more preferably an integer of about 50 to 1,000.

In the foregoing general formulae (2) and (3), "X" represents an oxygen atom or a divalent hydrocarbon group having 1 to 8 carbon atoms, and is preferably a group shown by —(CH$_2$CH$_2$)$_q$—, or —(CH=CH)$_q$— ("q" is 1 to 4). Among them, an oxygen atom, —CH$_2$CH$_2$—, and —CH=CH— are particularly preferable.

In the foregoing general formula (3), "Y'" represents a hydrolysable group, and can be the same hydrolysable group illustrated in the foregoing general formula (1), for example, alkoxy groups such as a methoxy group, an ethoxy group, a propoxy group, an isopropoxy group, a butoxy group, an isobutoxy group, a tert-butoxy group; alkoxyalkoky groups such as a methoxyethoxy group, an ethoxyethoxy group, a methoxypropoxy group; acyloxy groups such as an acetoxy group, an octanoyloxy group, a bezoyloxy group; alkenyloxy groups such as a vinyloxy group, an allyloxy group, a propenyloxy group, an isopropenyloxy group, a 1-ethyl-2-methylvinyloxy group; ketoxime groups such as a dimethylketoxime group, a methylethylketoxime group, a diethylketoxime group; amino groups such as a dimethylamino group, a diethylamino group, a butylamino group, a cyclohexylamino group; aminoxy groups such as a dimethyaminoxy group, a diethylaminoxy group; and amide groups such as an N-methylacetamide group, an N-ethylacetamide group, an N-methylbenzamide group. Among them, alkoxy groups are particularly preferable.

The organopolysiloxane of the component (B) preferably has a viscosity at 25° C. of 100 to 1,000,000 mPa·s, more preferably 300 to 500,000 mPa·s, particularly preferably 500 to 100,000 mPa·s, and especially 1,000 to 80,000 mPa·s. The above viscosity of the organopolysiloxane is preferable, because a coating film with excellent physical and mechanical strength can be obtained when the viscosity is 100 mPa·s or more; and the viscosity of the room-temperature-curable resin composition is not too high to deteriorate the workability during the use when the viscosity is 1,000,000 mPa·s or less. Herein, the viscosity is a value measured by a rotational viscometer (such as a BL type, a BH type, a BS type, and a cone and plate type).

As a specific example of the organopolysiloxane of the component (B), the following diorganopolysiloxanes are illustrated.

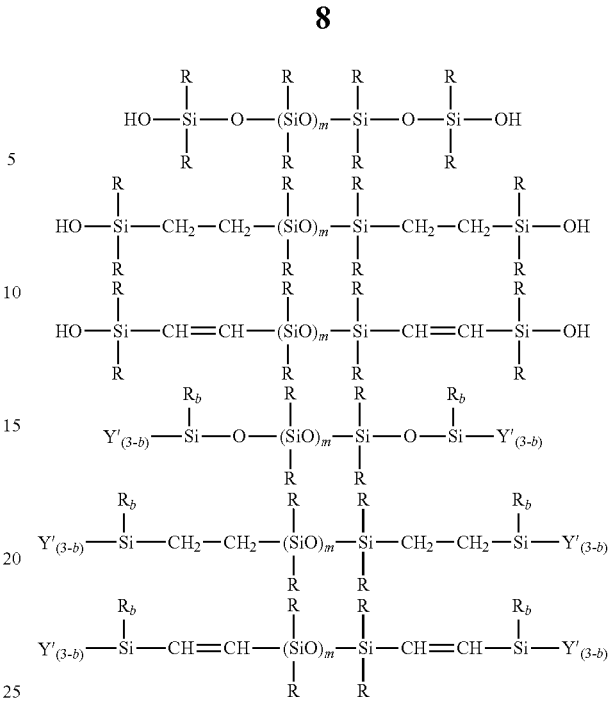

wherein, each of "R", "Y'", "b", and "m" has the same meaning as above.

The organopolysiloxane of the component (B) may be used alone or in combination of two or more kinds in which the structure or molecular weight are different from each other.

The inventive room-temperature-curable resin composition, which contains such an organopolysiloxane, can be a room-temperature-curable resin composition which is curable in shorter time; and has sufficient hardness, elongation at shear, and tensile strength after curing.

[Component (C)]

The component (C) is an optional component which can be formulated in accordance with needs. This is a curing catalyst except for the foregoing component (A), and is used in order to further reduce the curing time of the room-temperature-curable resin composition. Illustrative examples of such a catalyst include alkyltin ester compounds such as dibutyltin diacetate, dibutyltin dilaurate, dibutyltin dioctoate; titanate esters or titanium chelate compounds such as tetraisopropoxytitanium, tetra-n-butoxytitanium, tetrakis(2-ethylhexoxy)titanium, dipropoxybis(acetylacetonato)titanium, titanium isopropoxyoctyleneglycol; organometallic compounds such as zinc naphthenate, zinc stearate, zinc 2-ethyloctoate, iron 2-ethylhexoate, cobalt 2-ethylhexoate, manganese 2-ethylhexoate, cobalt naphthenate, an alkoxyaluminum compound, an aluminum chelate compound; aminoalkyl group-substituted alkoxysilane such as 3-aminopropyltriethoxysilane, N-β-(aminoethyl)-γ-aminopropyltrimethoxysilane; amine compounds and salts thereof such as hexyl amine, dodecylamine phosphate; quaternary ammonium salts such as benzyltriethylanmonium acetate; alkaline metal salts of short-chain fatty acid such as potassium acetate, sodium acetate, lithium oxalate; dialkylhydroxylamines such as dimethylhydroxylamine, diethylhydroxylamine; silanes and siloxanes having a guanidyl group such as tetramethylguanidylpropyltrimethoxysilane, tetramethylguanidylpropylmethyldimethoxysilane, tetramethylguanidylpropyltris(trimethylsiloxy)silane. They may be used alone or in combination of two or more kinds.

The formulation amount of these curing catalyst is preferably 0 to 15 parts by mass, particularly preferably 0.01 to 5 parts by mass based on 100 parts by mass of the foregoing organopolysiloxane of the component (B).

As described above, the inventive room-temperature-curable resin composition contains the phosphazene skeleton-containing organosilicon compound of the component (A) as a curing catalyst, and therefore the usage of an organotin compound can be reduced even if an organotin compound-containing curing catalyst of the component (C) is used. That is, the inventive composition can be a room-temperature-curable resin composition with reduced risk, toxicity, and odor due to an organotin compound.

[Component (D)]

The component (D): either or both of hydrolysable silane and a partial hydrolysis-condensate thereof except for the component (A) is an optional component which can be formulated in accordance with need, and functions as a crosslinker. The hydrolysable group can be the same hydrolysable group illustrated in the foregoing general formula (1) or (3). Illustrative examples thereof include a ketoxime group, an alkoxy group, an acetoxy group, and an isopropenoxy group; and an alkoxy group and an isopropenoxy group are preferable. As an example of the component (D), an organosilane compound having at least one, preferably two or more (more preferably, three or four) of these hydrolysable groups in the molecule and/or a partial hydrolysis-condensate thereof may be mentioned. In the present application, the partial hydrolysis-condensate means an organosiloxane oligomer which contains at least one, preferably two or more (more preferably, three or more) of remained hydrolysable group in the molecule obtained by (co)hydrolysis-condensation of one or plural of the hydrolysable silane(s).

Illustrative examples of the component (D) include alkoxysilanes such as metyltrimethoxysilane, dimetyldimethoxysilane, vinyltrimethoxysilane, phenyltrimethoxysilane, methyltriethoxysilane; isopropenoxy group-containing silanes such as metyltriisopropenoxysilane, ethyltriisopropenoxysilane, vinyltriisopropenoxysilane, phenyltriisopropenoxysilane; acetoxysilanes such as methyltriacetoxysilane, ethyltriacetoxysilane, vinyltriacetoxysilane; and partial hydrolysis-condensates of these silanes. They may be used alone or in combination of two or more kinds.

The formulation amount of the component (D) is generally 0 to 30 parts by mass, preferably 0.1 to 20 parts by mass, more preferably 0.5 to 15 parts by mass based on 100 parts by mass of the foregoing component (B). The formulation amount of 30 parts by mass or less is preferable, since the cured product does not come to be too hard, and it is economical.

[Component (E)]

The component (E) is a filler, an optional component which can be formulated in accordance with need, and is formulated to give the cured product formed from the composition sufficient mechanical strength. As this filler, any commonly known filler can be used, and illustrative examples thereof include reinforcing silica fillers such as fine powder silica, fumed silica, silica aerogel, precipitated silica; metal oxides such as diatomaceous earth, iron oxide, zinc oxide, titanium oxide or those having silane treated surface; metal carbonates such as calcium carbonate, magnesium carbonate, zinc carbonate; inorganic fillers such as asbestos, glass wool, carbon black, fine powder mica, fused silica powder (fine powder quartz); synthesized resin powder such as polystyrene, polyvinylchloride, polypropylene.

The formulation amount of the component (E) is preferably 0 to 1,000 parts by mass, particularly preferably 5 to 200 parts by mass based on 100 parts by mass of the foregoing component (B). The cured product obtained from the room-temperature-curable resin composition comes to have sufficient mechanical strength by formulating the component (E). When the formulation amount is 1,000 parts by mass or less, it is possible to avoid deterioration of workability due to an increase of a viscosity of the composition and deterioration of rubber elasticity due to lowering of the rubber strength after curing. The filler of the component (E) may be used alone or in combination of two or more kinds which are different from each other.

[Component (F)]

The component (F) is an adhesion promoter, an optional component which can be formulated in accordance with need. Illustrative examples thereof include so called carbon functional silane (silane coupling agent) such as alkoxysilanes having a monovalent hydrocarbon group which contains a functional group such as an epoxy group, an amino group, an isocyanate group, and (meth)acryloxy group; and/or hydrolysis-condensate thereof. It is particularly preferable to formulate aminosilanes such as γ-aminopropyltriethoxysilane, 3-2-(aminoethylamino)propyltrimethoxysilane; epoxysilanes such as γ-glycidoxypropyltrimethoxysilane, β-(3,4-epoxycyclohexyl)ethyltrimethoxysilane; and isocyanate silanes. The formulation amount of these adhesion promoter is preferably 0 to 30 parts by mass, particularly preferably 0.2 to 10 parts by mass based on 100 parts by mass of the foregoing organopolysiloxane of the component (B). The adhesion promoter of the component (F) may be used alone or in combination of two or more kinds which are different from each other.

Such an inventive room-temperature-curable resin composition which contains the components (A) to (F) can be a room-temperature-curable resin composition which is curable in shorter time, has an excellent adhesive property; and particularly gives an elastomer-like cured material such as silicone rubber having sufficient hardness, elongation at shear, and tensile strength after curing.

In addition to the components (A) to (F), it is possible to formulate additives commonly known such as pigments, dyes, antiaging agents, antioxidants, antistatic agent, flame retardants such as antimony oxide and chlorinated paraffin to the room-temperature-curable resin composition of the present invention. Furthermore, polyether as a thixotropy-enhancer, antifungal agents, antimicrobial agents, and adhesion aids can be formulated.

As described above, the room-temperature-curable resin composition of the present invention contains a phosphazene skeleton-containing organosilicon compound as a curing catalyst, and therefore can be a room-temperature-curable resin composition which is curable in short time, has low risk and toxicity due to the curing catalyst, does not generate odor due to the catalyst, since it contains no organotin compound or lower amount of organotin compound if it is contained, and gives a cured product having sufficient hardness, elongation at shear, and tensile strength, that is, rubber physical properties after curing.

Moreover, such inventive room-temperature-curable resin composition is suitable as a fast-curing resin, and can be suitably used for a coating agent, an adhesive, or a sealant.

EXAMPLE

Hereinafter, the present invention will be specifically described with reference to examples and comparative examples, but the present invention is not limited thereto. It is to be noted that the viscosity indicates a value measured with a rotational viscometer at 25° C.

Example 1

Under an atmosphere excluding the moisture, 100 parts by mass of linear dimethylpolysiloxane both terminals of which are blocked with trimethoxysilyl-ethylene groups, having a viscosity of 1,000 mPa·s, and 0.5 parts by mass of N,N,N',N',N",N"-hexamethyl-N'"-[3-(trimethoxysilyl)propyl]-phosphorimidictriamide were homogeneously mixed to prepare a room-temperature-curable resin composition (a room-temperature-curable silicone rubber composition).

Example 2

Under an atmosphere excluding the moisture, 100 parts by mass of linear dimethylpolysiloxane both terminals of which are blocked with trimethoxysilyl-ethylene groups, having a viscosity of 1,000 mPa·s, and 0.5 parts by mass of N,N,N',N',N",N"-hexaethyl-N'"-[3-(trimethoxysilyl)propyl]-phosphorimidictriamide were homogeneously mixed to prepare a room-temperature-curable resin composition (a room-temperature-curable silicone rubber composition).

Example 3

Under an atmosphere excluding the moisture, 100 parts by mass of linear dimethylpolysiloxane both terminals of which are blocked with trimethoxysilyl-ethylene groups, having a viscosity of 1,000 mPa·s, and 0.5 parts by mass of N,N,N',N',N",N"-hexamethyl-N'"-(trimethylsilylmethyl)-phosphorimidictriamide were homogeneously mixed to prepare a room-temperature-curable resin composition (a room-temperature-curable silicone rubber composition).

Comparative Example 1

Under an atmosphere excluding the moisture, 100 parts by mass of linear dimethylpolysiloxane both terminals of which are blocked with trimethoxysilyl-ethylene groups, having a viscosity of 1,000 mPa·s, and 0.5 parts by mass of 1,1,3,3,-tetramethyl-2-[3-(trimethoxysilyl)propyl]guanidine were homogeneously mixed to prepare a room-temperature-curable resin composition (a room-temperature-curable silicone rubber composition).

Comparative Example 2

Under an atmosphere excluding the moisture, 100 parts by mass of linear dimethylpolysiloxane both terminals of which are blocked with trimethoxysilyl-ethylene groups, having a viscosity of 1,000 mPa·s, and 0.5 parts by mass of 1,8-diazabicyclo[5.4.0]undec-7-ene were homogeneously mixed to prepare a room-temperature-curable resin composition (a room-temperature-curable silicone rubber composition).

(Tests)

On each room-temperature-curable resin composition (a room-temperature-curable silicone rubber composition) prepared in Examples 1 to 3 and Comparative Example 1 and 2, tack-free time was measured.

To measure the tack-free time, each room-temperature-curable resin composition immediately after the preparation was extruded into a sheet with a thickness of 2 mm; and while being exposed to the air at 23° C. and 50% RH (relative humidity), the surface of the sheet was touched to measure a time until the surface tackiness had completely disappeared.

Alternatively, each room-temperature-curable resin composition immediately after the preparation was extruded into a sheet with a thickness of 2 mm, exposed to the air at 23° C. and 50% RH, and then this sheet was left in the same condition for 7 days. The physical properties (hardness, elongation at shear, tensile strength) were measured on the obtained cured product of the silicone rubber composition in accordance with the method provided in JIS K-6249. Incidentally, the hardness was measured by using a Durometer A hardness meter in accordance with JIS K-6249 (initial physical properties).

Furthermore, the same measurements were performed on the silicone rubber cured product stored in a thermo-hygrostat at 85° C. and 85% RH for 100 hours (durability test). Moreover, the same measurements were performed on the silicone rubber sheet with a thickness of 2 mm which had been prepared by subjecting each room-temperature-curable resin composition prepared in Examples 1 to 3 and Comparative Example 1 and 2 to be left at 70° C. for 7 days in a closed container immediately after the preparation, and then to be exposed to the air at 23° C. and 50% RH for 7 days (storage test).

These results are shown in Table 1.

TABLE 1

| | | Example 1 | Example 2 | Example 3 | Comparative Example 1 | Comparative Example 2 |
|---|---|---|---|---|---|---|
| Initial physical properties | Tack-free time (min.) | 4 | 6 | 7 | 34 | 17 |
| | Hardness (Duro. A) | 29 | 26 | 29 | 25 | 26 |
| | Elongation at shear (%) | 59 | 71 | 66 | 65 | 76 |
| | Tensile strength (MPa) | 0.31 | 0.31 | 0.32 | 0.25 | 0.38 |
| Durability test 85° C., 85% RH | Hardness (Duro. A) | 25 | 19 | 30 | 23 | 26 |
| | Elongation at shear (%) | 85 | 84 | 55 | 85 | 80 |
| | Tensile strength (MPa) | 0.27 | 0.20 | 0.29 | 0.29 | 0.37 |
| Storage test 70° C., 7 days | Hardness (Duro. A) | 27 | 25 | 27 | 26 | 27 |
| | Elongation at shear (%) | 69 | 79 | 75 | 81 | 68 |
| | Tensile strength (MPa) | 0.33 | 0.35 | 0.28 | 0.29 | 0.35 |

As shown in Table 1, each composition of Examples 1 to 3, which contains a phosphazene skeleton-containing organosilicon compound shown by the foregoing general formula (1) as a curing catalyst, cured in shorter time compared to each composition of Comparative Examples 1 and 2, which did not contain the phosphazene skeleton-containing organosilicon compound as a curing catalyst. Furthermore, each cured product of Examples 1 to 3 had hardness, elongation at shear, and tensile strength equivalent to each cured product of Comparative Examples 1 and 2, that is, sufficient rubber physical properties, in spite of being cured in shorter time. Moreover, the rubber physical properties were not largely deteriorated after the durability test and the storage test.

From the foregoing, it has revealed that the room-temperature-curable resin composition of the present invention can be a room-temperature-curable resin composition which is curable in short time, free from generation of an odor due to the catalyst, free from a heavy environmental load; and has sufficient hardness, elongation at shear, and tensile strength, that is, rubber physical properties after curing by containing a particular phosphazene skeleton-containing organosilicon compound as a curing catalyst.

It is to be noted that the present invention is not limited to the foregoing embodiment. The embodiment is just an exemplification, and any examples that have substantially the same feature and demonstrate the same functions and effects as those in the technical concept described in claims of the present invention are included in the technical scope of the present invention.

The invention claimed is:

1. A room-temperature-curable resin composition comprising a phosphazene skeleton-containing organosilicon compound shown by the following general formula (1),

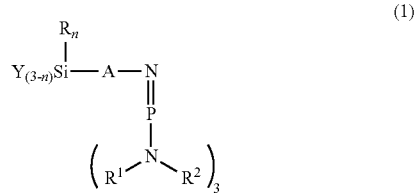

(1)

wherein, "R" represents a substituted or unsubstituted monovalent hydrocarbon group having 1 to 12 carbon atoms, "$R^1$" and "$R^2$" may be the same or different and represent a substituted or unsubstituted monovalent hydrocarbon group having 1 to 12 carbon atoms, "A" represents a single bond or a divalent hydrocarbon group having 1 to 6 carbon atoms, "Y" represents a hydrolysable group, and "n" is an integer satisfying $0 \leq n \leq 3$.

2. The room-temperature-curable resin composition according to claim 1, wherein the composition comprises an organopolysiloxane.

3. The room-temperature-curable resin composition according to claim 2, wherein the composition comprises:
   (A) 0.001 to 20 parts by mass of the phosphazene skeleton-containing organosilicon compound shown by the foregoing general formula (1);
   (B) 100 parts by mass of the organopolysiloxane;
   (C) 0 to 15 parts by mass of a curing catalyst except for the component (A);
   (D) 0 to 30 parts by mass of either or both of hydrolysable silane and a partial hydrolysis-condensate thereof except for the component (A);
   (E) 0 to 1,000 parts by mass of a filler; and
   (F) 0 to 30 parts by mass of an adhesion promoter.

4. The room-temperature-curable resin composition according to claim 1, wherein the composition is used for any of a coating agent, an adhesive, and a sealant.

5. The room-temperature-curable resin composition according to claim 2, wherein the composition is used for any of a coating agent, an adhesive, and a sealant.

6. The room-temperature-curable resin composition according to claim 3, wherein the composition is used for any of a coating agent, an adhesive, and a sealant.

* * * * *